United States Patent [19]
Baxter et al.

[11] Patent Number: 5,332,743
[45] Date of Patent: Jul. 26, 1994

[54] BENZYL AND BENZHYDRYL ALCOHOLS

[75] Inventors: Ellen W. Baxter; Allen B. Reitz, both of Lansdale, Pa.

[73] Assignee: McNeilab, Inc., Spring House, Pa.

[21] Appl. No.: 897,487

[22] Filed: Jun. 12, 1992

[51] Int. Cl.$^5$ ............... A61K 31/495; A61K 31/445; C07D 295/096; C07D 211/12

[52] U.S. Cl. .................... 514/255; 514/254; 514/317; 514/331; 544/392; 544/394; 544/362; 544/363; 544/368; 544/370; 544/371; 544/373; 544/376; 544/377; 546/196; 546/197; 546/198; 546/199; 546/200; 546/201; 546/202; 546/229; 546/230; 546/232

[58] Field of Search ................ 544/394; 514/255

[56] References Cited

U.S. PATENT DOCUMENTS

| | | |
|---|---|---|
| 3,819,707 | 6/1974 | Archer et al. .............. 544/394 |
| 3,950,393 | 4/1976 | Keck et al. .............. 544/81 |
| 4,515,793 | 5/1985 | Werbel et al. .............. 544/394 |
| 4,696,920 | 9/1987 | Bentzen et al. .............. 544/392 |

Primary Examiner—Emily Bernhardt
Attorney, Agent, or Firm—Ralph R. Palo

[57] ABSTRACT

Compounds of the general formula I:

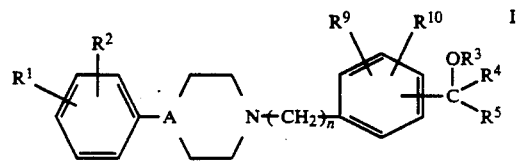

are disclosed as potent antipsychotic agents. Novel methods of use and intermediates used to make the compounds of formula I are also disclosed.

20 Claims, No Drawings

5,332,743

BENZYL AND BENZHYDRYL ALCOHOLS

BACKGROUND OF THE INVENTION

Antipsychotic drugs are known to alleviate the symptoms of mental illnesses such as schizophrenia. Examples of such drugs include phenothiazine derivatives such as promazine, chlorpromazine, fluphenazine, thioridazine and promethazine, thioxanthenes such as chlorprothixene, butyrophenones such as haloperidol, and clozapine. While these agents may be effective in treating schizophrenia, virtually all except clozapine produce extrapyramidal side effects, such as facial tics. Since antipsychotics may be administered for years or decades to a patient, such pronounced side effects may complicate recovery and further isolate the individual from society.

Compound having some structural similarity to those of the present invention are described in application Ser. No. 757,881 assigned to the same company as the present application and U.S. Pat. Nos. 3,950,393 and 4,696,920, as well as R. Coombs, W. J. Houlihan, J. Nadelson and E. I. Taskesue *J. Med. Chem.*, 1971, 14, 1072.

The present invention is directed to novel compounds and methods of use, which compounds have demonstrated antipsychotic activity.

SUMMARY OF THE INVENTION

Compounds of the general formula I:

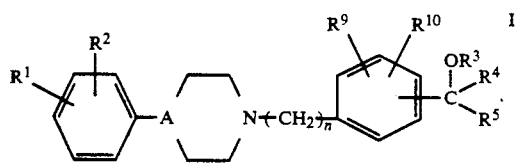

wherein $R^1$, $R^2$, $R^3$, $R^4$, $R^5$, $R^9$ and $R^{10}$ are as defined hereinafter, are disclosed as potent antipsychotic agents and may exhibit activity in other therapeutic areas. The present invention is also directed to novel methods of use for the compounds of the formula I and novel intermediates used to make such compounds.

DETAILED DESCRIPTION OF THE INVENTION

More particularly, the present invention is directed to compounds represented by the general formula I:

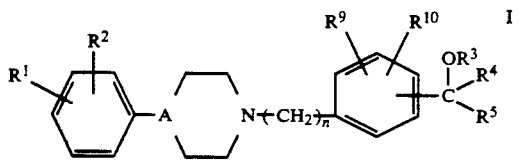

$R^1$ and $R^2$ are preferably independently selected from any of H, $C_1$-$C_8$ alkyl, $C_4$-$C_{10}$ cycloalkyl, $C_2$-$C_6$ hydroxyalkyl, $C_1$-$C_8$ alkoxy, aryloxy, hydroxyl, trifluoromethyl, trifluoromethoxy, cyano, $C_1$-$C_8$ alkylthio, halogen, nitro, $C_1$-$C_8$ haloalkyl, amino or $C_1$-$C_8$ mono- or di-alkylamino, with the proviso that $R^1$ and $R^2$ are not both H at the same time. Alkoxy such as i-propoxy and methoxy are presently the most preferred substituents. The preferred halogen atom is any of fluorine, chlorine, or bromine. The hydroxyl or hydroxyalkyl groups may be esterified or etherified.

$R^1$ and $R^2$ may also be combined together with the attached aromatic ring to form a fused ring system of the formula II:

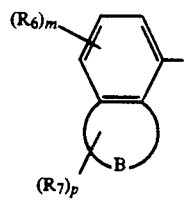

wherein B together with the 2 carbon atoms of the phenyl group forms an entirely or partly unsaturated cyclic group having 5–7 ring atoms and, within the ring 1–3 hetero atoms from the group O, S and N may be present, with the proviso that the sum of the number of oxygen atoms and sulfur atoms is at most 2, and that the nitrogen atoms in the ring may be substituted with $R_8$ selected from any one of H, $C_1$-$C_8$ alkyl, $C_1$-$C_8$ hydroxyalkyl or $C_1$-$C_8$ acyl;

$R^6$ and $R^7$ are independently selected from any one of alkyl, cycloalkyl, optionally substituted phenyl or heteroaryl, hydroxyalkyl, alkoxyalkyl, alkoxy, aryloxy, alkylthio, arylthio, mono-or di-alkylamino, mono-or di-arylamino, hydroxyl, amino, alkyl, alkoxy, amino, or mono- or di-alkylaminocarbonyl, nitro, cyano, halogen, trifluoromethyl, trifluoromethoxy, amino or mono- or di-alkylaminosulbonyl.

Variable m has the value 0–3 and p has the value 0–2.

More preferred values for the moiety of formula II are:

B forms together with the two carbon atoms of the phenyl group an entirely or partly unsaturated ring consisting of 5 atoms, which ring comprises at least one oxygen atom. $R^6$ and $R^7$ are alkyl, alkoxy, hydroxyl, nitro, cyano, halogen, or trifluoromethyl. m and p have the value 0–2.

When $R^6$ or $R^7$ comprises an alkyl group or a substituent containing an alkyl group, it is preferably a straight or branched alkyl group having 1–5 carbon atoms unless otherwise noted. As a cycloalkyl group, the groups $R^6$ or $R^7$ comprise a ring system having 3–7 ring atoms and not more than 10 carbon atoms including any substituents as a whole. When $R^6$ or $R^7$ is a hydroxyalkyl group the alkyl group preferably comprises 1–5 carbon atoms. As a halogen atom, $R^6$ or $R^7$ preferably is fluorine, chlorine or bromine. Optionally present hydroxyl or hydroxyalkyl groups may be esterified or etherified.

A is either CH or N, but most preferably N.

$R^3$ is selected from any of H, $C_1$-$C_8$ acyl, $C_1$-$C_8$ alkyl, $C_4$-$C_8$ cycloalkyl, or aralkyl.

$R^4$ and $R^5$ are independently selected from any of H, $C_1$-$C_8$ alkyl, phenyl, substituted phenyl, aralkyl, $C_4$-$C_8$ cycloalkyl.

$R^4$ and $R^5$ may also be taken together to form a ring having 4–10 ring atoms, which ring may be saturated or unsaturated, preferably saturated, substituted or unsubstituted, and may contain up to 2 hetero atoms such as S, O or N within the ring. $R^4$ and $R^5$ are preferably independently selected from any of phenyl, $C_1$-$C_5$ alkyl or cyclohexyl and most preferably from either of phenyl or $C_1$-$C_5$ alkyl.

$R^9$ and $R^{10}$ are independently selected from any one of H, $C_1$-$C_8$ alkyl, $C_1$-$C_8$ alkoxy, nitro, halogen, haloalkyl, $C_1$-$C_8$ alkylthio, amino, or $C_1$-$C_8$ mono-or di-alkyl amino. Preferably each of $R^9$ and $R^{10}$ are H.

In the cases wherein there is a substituted phenyl or substituted aryl, the substitution is with one or more of $C_1$-$C_8$ alkyl, $C_1$-$C_8$ alkoxy, halogen, trifluoromethyl, $C_1$-$C_8$ alkylthio, dialkylamino (wherein each alkyl is $C_1$-$C_8$), $C_1$-$C_8$ alkylamino, nitro, or mono- or di-alkylamino sulfonyl (wherein each alkyl is $C_1$-$C_8$).

Variable n has the value of 1-4. Preferably n has a value of one.

As used herein unless otherwise noted alkyl and alkoxy include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 3-methylpentyl. Alkoxy radicals are oxygen ethers formed from the previously described straight or branched chain alkyl groups.

The term "aryl" as used herein alone or in combination with other terms indicates aromatic hydrocarbon groups such as phenyl or naphthyl. The term "heteroaryl" means aromatic systems containing one or more atoms chosen from N, S, Se and P. The term "aralkyl" means a radical containing a $C_1$-$C_8$ alkyl groups substituted with an aryl radical or substituted aryl radical. With reference to substituents, the term independently means that when more than one of such substituent is possible such substituents may be the same or different from each other.

Compounds according to this invention including the intermediate compounds have a 1,3- or 1,4- relationship of the $C(OR^3)R^4R^5$ substituent or intermediate related substituent with the $-CH_2-$ group on the $C(OR^3)R^4R^5$ or intermediate related substituent-bearing phenyl ring. The structural formulas herein include both structural relationships.

A particularly preferred subgenus is the compound of the formula I(a):

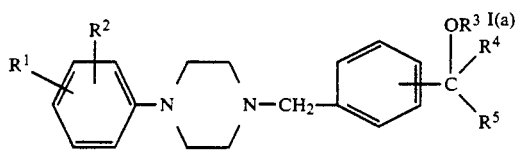

wherein $R^1$ and $R^2$ are any of the substituents listed in the first paragraph after formula I in this Detailed Description and $R^3$, $R^4$ and $R^5$ are as previously described.

Examples of particularly preferred compounds include:
3-[4-[2-(1-Methylethoxy)phenyl]-1-piperazinylmethyl]-α-phenylbenzenemethanol;
4-[4-[2-(1-Methylethoxy)phenyl]-1-piperazinylmethyl]-α-phenylbenzenemethanol;
3-[4-[2-(1-Methylethoxy)phenyl]-1-piperazinylmethyl]-α-methyl-α-ethylbenzenemethanol; and
1-(3-Acetoxymethylphenyl)methyl-4-[2-(1-methylethoxy)phenyl]-piperazine.

The definition of formula I includes racemates and individual isomers; e.g., as caused by the presence of an asymmetric carbon such as when a substituent would be 2-butyl. Also within the scope of the invention are compounds of the invention in the form of hydrates and other solvate forms.

Representative salts of the compounds of formula I which may be used include those made with acids such as hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, ethanesulfonic, hydroxyethanesulfonic, benzenesulfonic, p-toluenesulfonic, cyclohexanesulfamic, salicyclic, p-amino-salicyclic, 2-phenoxybenzoic, 2-acetoxybenzoic or a salt made with saccharin. Such salts can be made by reacting the free base of formula I with the acid and recovering the salt.

The compounds of formula I may be prepared according to the Reaction Scheme 1, where all of the variable groups are as defined for Formula I:

· Reaction Scheme 1

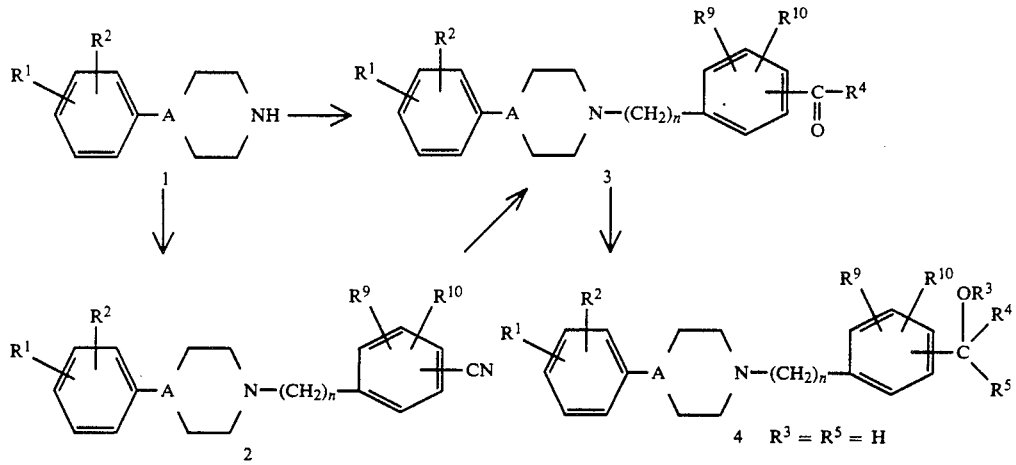

Aryl piperazines or piperidines 1 can be reacted with a haloalkylbenzonitrile to give compound 2, or with an (haloalkyl)-alkanophenone or -benzophenone to give compound 3. These reactions can be carried out in either THF or a dipolar aprotic solvent such as DMSO or DMF, in the presence of a base such as triethyl amine or $K_2CO_3$, generally requiring heating of from about 30°-80° C. The requisite haloalkylbenzonitriles or (haloalkyl)-alkanophenones or -benzophenones are generally available following literature procedures or modifications thereof. Treatment of nitriles 2 with Grignard reagents followed by treatment with cold aqueous HCl, and stirring for a prolonged period (5-30 h) at about room temperature (5–30 h) results in the compounds 3. Reduction of compound 3 by chemical means, such as with sodium borohydride, gives compound 4, which is a subclass of the compound of formula I wherein $R^3$ and $R^5$ are H. In Reaction Scheme 1, there is a 1,3 or 1,4 arrangement of the CN, $C(O)R^4$, or $C(OR^3)R^4R^5$ substituent, on that aromatic ring which is on the right as drawn in 2, 3, and 4, with respect to the $CH_2$ group also attached to the ring.

Alternatively, certain compounds of the invention (n=1) can be prepared by the method shown in Reaction Scheme 2.

would occur by heating 5 in a dipolar aprotic solvent such as DMSO or DMF in the presence of an alkoxide anion such as sodium ethoxide. It is clear from Reaction Scheme 2 that compounds 10 where $R^3$ are acyl can also be made from 5 by displacement of the chloride of 5 with suitable acylate nucleophiles.

Reaction Scheme 3

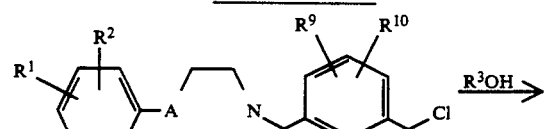

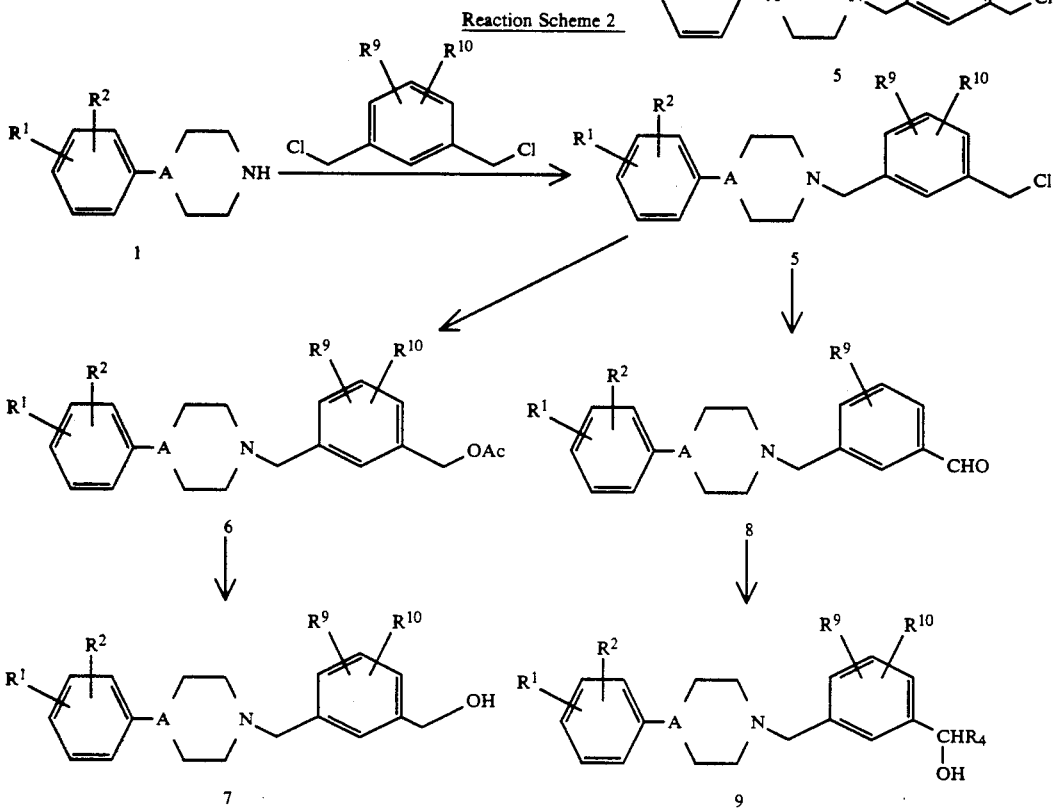

Aryl piperazines or piperidines 1 can be condensed with meta-xylylene dichloride to give compounds 5. This reaction was carried out with a 3-fold excess of meta-xylylene dichloride. The yield is reproducibly 60–70%, and the hydrochloride salt can be readily obtained directly from the reaction. This compound can then undergo displacement with acetate anion to give compound 6. This reaction can be carried out by heating a solution of 5 with potassium acetate and a crown ether (18-crown-6) in acetonitrile. Basic hydrolysis (KOH, MeOH, reflux) can be used to cleave the acetyl group to give compound 7. Alternatively, compound 5 can be subjected to a Kornblum oxidation ($NaHCO_3$, DMSO, heating) to give compound 8, which is a versatile intermediate for the preparation of compounds of formula I of type 9. Although the reactions shown in Reaction Scheme 2 are particular for the 1,3 substitution pattern on the right aromatic ring as drawn, this chemistry can be extended to the 1,4 substitution pattern.

Additional compounds of the present invention can be made by taking compound 5 and displacing the chlorine with the anion of an alcohol to give an ether type linkage as shown in Reaction Scheme 3. Such reactions In the cases where $R^3$ is acyl or alkyl, these compounds can be prepared by taking alcohols such as 4,7, 9, or similar compounds, except with 1,4 substitution patterns, and then treating them with acylating reagents, such as acid chlorides, or alkylating reagents, such as alkyl iodides or alkyl sulfonates, under the appropriate conditions known in the art.

Those examples of 1 which are aryl piperazines, excepting those wherein $R^1$ and $R^2$ are of formula II, are commercially available from the Aldrich Chemical Company or another fine chemical supplier, or may be prepared by standard methods known in the art. See for example, G. E. Martin et al. *J. Med. Chem.* 1989, 32, 1052. These piperazines may be obtained according to the following Reaction Scheme 4 where $R^1$ and $R^2$ are as described for formula I and Z is a leaving group such as halo (e.g. chloro):

Reaction Scheme 4

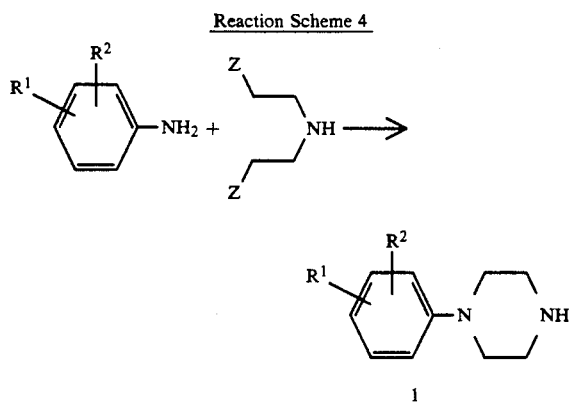

In carrying out Reaction Scheme 4, the two reaction components are reacted at about 50° C. to 150° C. in a solvent such as n-butanol with recovery of the piperazine 1.

Piperazines of type 1 wherein $R^1$ and $R^2$ are of formula II are disclosed as formula (2) in U.S. Pat. No. 4,782,061 and may be prepared as described therein, the disclosure of which is incorporated herein by reference. Other piperazines of type 1 where $R^1$ and $R^2$ are of formula II are described as formula 29 in EPO 138,280 published Apr. 24, 1985.

In the instances in which 1 are aryl piperidines, these can be prepared by the method shown in Reaction Scheme 5, or variations of this method.

and 1,4 substitution pattern mentioned previously in connection with the compound of formula I.

To prepare the pharmaceutical compositions of this invention, one or more compounds or salts thereof of the invention, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain per dosage unit; e.g., tablet, capsule, powder, injection, teaspoonful and the like, from about 50 to about 100 mg of the active ingredient.

The antipsychotic activity of the compounds of the present invention was determined by the block of Conditioned Avoidance Responding (Rat) test (CAR), references being Cook, L. and E. Weidley in *Ann N.Y. Acad. Sci.*, 1957, 6, 740–752, and Davidson, A. B. and E.

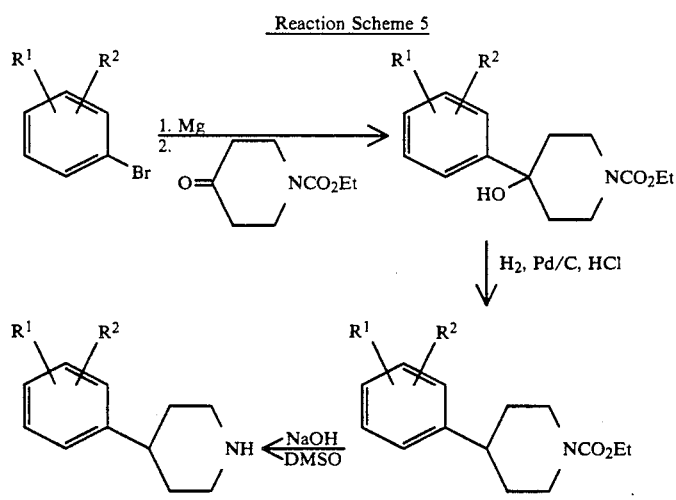

Reaction Scheme 5

The final products are preferably chromatographed to achieve purity, and then converted to an acceptable salt form.

The present invention is also directed to novel intermediates of formulas 3 and 5 of Reaction Schemes 1 and 2, which are useful in making the compounds of formula I. Both compounds include compounds having the 1,3

Weidley in *Life Sci.*, 1976, 18, 1279–1284. This test was performed for compounds disclosed in this invention, and the data are listed in Table 1. In addition, the affinity of the compounds for several receptors found in the central nervous system was evaluated. The affinity for the D-2 (dopamine-2) receptors is also listed in Table 1. Table 1 appears after the Examples. As modulation of the D2 receptor is known to be beneficial in the treatment of schizophrenia, affinity for this receptor indicates potential utility for the compounds.

Block of Conditioned Avoidance Responding (Rat)

Apparatus: Rat operant chambers, housed within sound attenuated booths, both from Capden Instruments Ltd., were used in this test. The test chamber (8" H×90-⅛" W×9" D) is constructed of aluminum and plexiglass with floor grid bars of stainless-steel (⅛" O.D.) spaced 9/16" apart. A stainless-steel operation level 1-½" wide projects ⅜" into the chamber and is positioned 2-2/8" above the grid floor. The shock stimulus is delivered via the grid floor by a Coulbourn Instruments solid state module. The parameters of the test and the collection of data are controlled automatically.

Training: Male, Fischer 344 rats obtained from Charles River (Kingston, N.Y.) weighing more than 200 g, are individually housed with chow and water provided ad libitum. The rats are trained for two weeks to approach criterion levels in the avoidance test (90% avoidance rate). One-hour training sessions are run at about the same time each day for four or five days a week. The training session consists of 120 trials, with the conditioned stimuli presented every 30 seconds. A trail begins with presentation of the conditioned stimuli (a light and a tone). If the rat responds by depressing the operant lever during the 15-second presentation of the conditioned stimuli, the trial is terminated and the animal is credited with a CAR. Failure to respond during the conditioned stimuli causes the presentation of the unconditioned stimulus, a 0.7 mA shock which is accompanied by a light and tone for five seconds. If the rat depressed the lever within the ten-second period, the shock and trial are terminated and an escape response recorded. If the rat fails to depress the lever during the UCS (shock), the trial is terminated after ten seconds of shock and the absence of a response is scored as a failure to escape. Intertrial level presses have no effect. If a rat performs at the 90% CAR level for two weeks, it is then run twice a week o the test schedule (see below) until baseline performance stabilized. Before any drug is administered, two weeks of CAR at a rate of 90% or better is required.

Statistical Computations: $ED_{50}$ values (that dose required to reduce the mean number of CARs to 50% of the control mean) are determined in the following manner. The percent change in CAR on the drug treatment day compared to vehicle pretreatment day is the key measure. The percent change (% change) in CAR is determined using the following formula:

% change $CAR = ((Day\ 2\%\ CAR/Day\ 1\%\ CAR) \times 100) - 100$

A negative number indicates a blockade of CAR, whereas a positive number would indicate increased CAR. The test results are reported as the mean % change for the group of rats. A reading of −20% is generally taken to represent a minimum value for a compound to be designated as active at a given dose in the CAR test. Failure to escape was calculated for each animal as follows:

% Failures = # of Failures to Escape/# of trials

The % failures, viz., loss of escape, is also reported as a group mean. Failures to escape are monitored closely and a session is terminated if ten failures occurred. $ED_{50}$ values and 95% confidence limits are calculated using linear regression analysis. The results of the CAR test is shown in Tables I.

The escape loss numbers are shown at CAR 5 mg/kg.

Receptor Binding Assay

The dopamine $D_2$ binding activity of compounds was determined using a $P_2$ fraction (synaptosomal membranes) prepared from male, Wistar rats. The $D_2$ assay employed a $P_2$ fraction from the striatum, the ligand $^3$H-spiperone at a concentration of 0.05 nM, and 1 mM haloperidol as a blank determinant. Incubation was in 3 mM potassium phosphate buffer for 45 min at 37° C. Under these conditions, specific binding constituted 75% of total binding, and the $K_i$ values for some known drugs were: 0.37 nM for haloperidol and 82 nM for clozapine.

The data from this assay were analyzed by calculating the percent inhibition of the binding of the tritiated ligands by given concentrations of the test compound. $K_i$ values, where given, were obtained from the logit analysis of concentration-inhibition curves.

The following Examples illustrate the present invention, but are not deemed to be limiting. The compound numbers in the Examples are to be taken to be the same as those listed in Table 1, and not the Reaction Schemes. In Table 1, OiPr is isopropoxy and OMe is methoxy. Ph is phenyl. Me is methyl. Et is ethyl. iPr is isopropyl. cHx is cyclohexyl. Ac is acetyl.

SPECIFIC EXAMPLES

EXAMPLE 1

[3-[4-[2-(1-Methylethoxy)phenyl]-1-piperazinyl]methyl]-α-phenyl-benzenemethanol (1)

The free base of 2-isopropoxyphenyl piperazine was prepared by treatment of the fumarate salt with aqueous bicarbonate followed by extraction into chloroform, to provide a brown oil (7.28 g, 33.0 mmol) which was dissolved in 75 mL of tetrahydrofuran. To this solution was added a solution of 3-(bromomethyl)benzophenone (10.0 g, 3.63 mmol) in 75 mL of tetrahydrofuran followed by triethylamine (5.53 mL, 39.6 mmol). The reaction mixture was refluxed for 19 h. After cooling to ambient temperature the reaction mixture was poured into 1N HCl solution. After washing with ether, the aqueous solution was basified with solid $K_2CO_3$ and extracted with chloroform. The chloroform extracts were combined, dried ($Na_2SO_4$), and concentrated to provide a dark brown oil which was purified on a Waters 500A Prep LC apparatus (1% hexanes-chloroform) to afford 9.09 g of pure benzophenone intermediate as a brown oil. The oil was dissolved in acetone and treated with concentrated HBr (2.5 mL). When diethyl ether was added, a fine white precipitate fell out of solution. This solid was recrystallized from acetone/ether to provide 4.59 g of a white solid. A second crop of crystals was also collected. These were combined to provide 7.94 g (46%) of aryl piperazine benzophenone intermediate, mp 193°–197° C. The $^1$H NMR in $CD_3OD$ supported the assigned structure.

Elemental analysis: Calculated for $C_{27}H_{30}N_2O_2 \cdot 1.4$ HBr: C, 61.44; H, 6.00; N, 5.31; Br, 21.19. Found C, 61.02; H, 5.99; N, 5.17; Br, 20.63.

The free base of the benzophenone described above was prepared by treatment with aqueous bicarbonate followed by extraction into chloroform, giving an orange-brown oil (3.30 g, 7.96 mmol) which was dissolved in 125 mL of absolute ethanol followed by the addition of $NaBH_4$ (0.36 g, 9.55 mmol). After 6 h of stirring under nitrogen, the reaction mixture was cooled in ice and 15 mL of cold 1N HCl solution was added. After 1 min of stirring, the reaction mixture was basified with solid $K_2CO_3$ and extracted with chloroform. The combined chloroform extracts were combined, dried ($Na_2SO_4$), and concentrated to provide a waxy white solid. Recrystallization from diethyl ether afforded 2.50 g (75%) of benzhydryl alcohol 1 as white crystals, mp 139°–142° C. The $^1H$ NMR in $CDCl_3$ supported the assigned structure.

Elemental analysis: Calculated for $C_{27}H_{32}N_2O_2$: C, 77.85; H, 7.74; N, 6.72. Found C, 77.35; H, 7.70; N, 6.62.

EXAMPLE 2

[3-[4-[2-(1-Methylethoxy)phenyl]-1-piperazinyl]methyl]-α-methyl-benzenemethanol (2)

The free base of 2-isopropoxyphenyl piperazine was prepared by treatment of the fumarate salt with bicarbonate followed by extraction to provide a brown oil (26.0 g, 121 mmol) which was dissolved in 150 mL of tetrahydrofuran. This solution was added over 30 min to a solution of 1,3-di(chloromethyl)benzene (63.8 g, 364 mmol) and triethylamine (20.3 mL, 146 mmol) in 150 mL of tetrahydrofuran. The reaction mixture was refluxed under argon for 1.5 h and then cooled to ambient temperature overnight. The reaction mixture was filtered, and the filtrate was concentrated and then diluted with diethyl ether followed by the addition of 3N HCl. The resulting suspension was filtered to provide 31.2 g (67%) of 1-(3-chloromethylphenyl)-4-[2-(1-methylethoxy)phenyl]piperazine hydrochloride.

To a solution of sodium bicarbonate (15.9 g, 190 mmol) in 100 mL of dimethylsulfoxide at 110° C. was added the arylpiperazine prepared above (10.0 g, 25.3 mmol) in 50 mL of dimethylsulfoxide. The reaction mixture was heated at 110° C. for 25 h. After cooling, the reaction mixture was partitioned between ether and water. The layers were separated and the aqueous layer was further extracted with ether. The combined ether extracts were washed with brine, dried ($MgSO_4$), and concentrated to afford an oil which was dissolved in ether followed by the addition of ethereal HCl. The resulting slurry was filtered and the resulting solid was partitioned between methylene chloride and saturated aqueous bicarbonate solution. The aqueous layer was extracted with dichloromethane. The combined organic extracts were washed with brine, dried ($MgSO_4$), and concentrated to give an oil. Purification by flash silica gel chromatography (9:1 to 87:13 hexanes/acetone) afforded an oil which was triturated with ethereal HCl to provide 5.6 g (60%) of aldehyde intermediate as a monohydrochloride salt.

The free base of the arylpiperazine aldehyde described above was prepared by treatment of the hydrochloride salt with bicarbonate followed by extraction into chloroform to provide a brown oil (1.90 g, 5.61 mmol) which was dissolved in 120 mL of anhydrous ethyl ether and cooled to 0° C. To this mixture was added dropwise a solution of methylmagnesium bromide in ethyl ether (2.30 mL, 2.9M). The reaction mixture was kept at 0° C. for 1 h and then was warmed to ambient temperature. After 15 h of stirring under nitrogen, the reaction mixture was cooled in an ice bath and saturated ammonium chloride solution was added. After neutralization with solid sodium bicarbonate, the mixture was extracted with chloroform. The chloroform extracts were combined, dried ($Na_2SO_4$), and concentrated to provide a light brown oil. This material was dissolved in methanol, and HCl (1.0 mL) was added. When ethyl ether was added, a cream-colored precipitate came out of solution. Recrystallization from methanol/ether provided 1.33 g (55%) of alcohol 2 as cream-colored granules, mp 184°–194° C. The $^1H$ NMR in $D_2O$ supported the assigned structure.

Elemental analysis: Calculated for $C_{22}H_{30}N_2O_2 \cdot 2HCl \cdot 0.1H_2O$: C, 61.56; H, 7.56; N, 6.53; Cl, 16.57; $H_2O$, 0.42. Found C, 61.92; H, 7.70; N, 6.57; Cl, 16.22; $H_2O$, 1.67.

EXAMPLE 3

1-(3-Acetoxymethylphenyl)methyl-4-[2-(1-methylethoxy)phenyl]-piperazine. (3)

The free base of 1-(3-chloromethylphenyl)-4-[2-(1-methylethoxy)phenyl]piperazine (described in Example 2) was prepared by treatment of the hydrochloride salt with bicarbonate to provide a brown oil (5.50 g, 13.9 mmol) which was dissolved in 70 mL of acetonitrile. To this solution was added potassium acetate (2.73 g, 27.8 mmol) and 18-crown-6 (0.18 g, 0.70 mmol). The reaction mixture was refluxed under argon for 4 h. The reaction mixture was concentrated in vacuo and the residue was partitioned between dichloromethane and water. The layers were separated and the aqueous layer was extracted with dichloromethane. The organic extracts were combined, washed with brine, and dried ($MgSO_4$). The organic layer was concentrated, and the residue was taken up in ethyl ether. This solution was added to ethereal HCl. The resulting precipitate was collected, washed with ethyl ether, and dried under vacuum to provide 5.3 g (90%) of acetate dihydrochloride 3, mp 174° C. (dec). The $^1H$ NMR supported the desired structure.

Elemental analysis: Calculated for $C_{23}H_{30}N_2O_3 \cdot 2.0HCl \cdot 0.5H_2O$: C, 59.48; H, 7.16; N, 6.03; Cl, 15.27; $H_2O$, 1.94. Found C, 59.80; H, 7.11; N, 6.03; Cl, 15.30; $H_2O$, 2.20.

EXAMPLE 4

1-(3-Hydroxymethylphenyl)methyl-4-[2-(1-methylethoxy)phenyl]-piperazine (4)

To a solution of 85% KOH (0.5 g, 7.57 mmol) in 50 mL of methanol was added compound 3 (2.50 g, 5.97 mmol). After overnight stirring, thin layer chromatography indicated very little reaction progress so the reaction mixture was refluxed under argon for several minutes. Chromatographic analysis still indicated little reaction progress so the reaction mixture was cooled. Additional KOH (0.53 g) was added and reflux was continued another 15 minutes. After this period of time, the starting material was completely consumed. The reaction mixture was concentrated, and the residue was partitioned between methylene chloride and water. The layers were separated, and the aqueous layer was further extracted with methylene chloride. The organic extracts were combined, washed with brine, and dried ($MgSO_4$). The organic extract was concentrated to provide an oil which was dissolved in isopropanol and filtered through $MgSO_4$. To the filtrate was added maleic acid (0.725 g), and the resulting mixture was concentrated in vacuo to provide an oil which was partitioned between 3N NaOH and methylene chloride. The layers were separated and the aqueous layer was extracted with dichloromethane. The organic extracts were combined, washed with brine, and dried ($MgSO_4$).

The organic extract was concentrated, and the resulting oil was purified on TLC mesh silica (97:3 methylene chloride:methanol). The purified material was dissolved in ethyl ether and added to ethereal HCl. The resulting precipitate was collected by suction filtration and washed with ether. The sample was dried to provide 1.72 g (70%) of benzyl alcohol dihydrochloride 4, mp 201° C. (dec). The $^1$H NMR supported the desired structure.

Elemental analysis: Calculated for $C_{21}H_{28}N_2O_2 \cdot 2.0HCl$: C, 61.02; H, 7.31; N, 6.78. Found C, 60.87; H, 7.25; N, 6.78.

EXAMPLE 5

[3-[4-(2-Methoxyphenyl)-1-piperazinyl]methyl]-α-phenylbenzenemethanol (5)

The free base of 2-methoxyphenyl piperazine was prepared by treatment of the hydrochloride salt with bicarbonate followed by extraction into methylene chloride to provide a brown oil (58.0 g, 302 mmol) which was dissolved in 650 mL of tetrahydrofuran. To this solution was added 3-cyanobenzyl bromide (70.8 g, 0.362 mol) and triethylamine (54.7 mL, 0.362 mol). The resulting suspension was refluxed for 20 h. After cooling, the reaction mixture was poured into 1N HCl solution. The resulting solution was washed with ether, basified with solid $K_2CO_3$, and extracted with chloroform. The chloroform extracts were combined, dried ($Na_2SO_4$), and concentrated to provide a golden brown oil. Purification on a Waters Delta Prep 3000 LC apparatus afforded 89.3 g (93%) of a golden brown solid whose spectral properties were consistent with the desired structure.

To an ice-cooled solution of 1-(3-cyanobenzyl)-4-(2-methoxyphenyl)piperazine (16.5 g, 53.7 mmol) in 800 mL of tetrahydrofuran was added a solution of phenylmagnesium bromide in ethyl ether (53.6 mL, 3.0M) under nitrogen. The solution was slowly warmed to 25° C. and then brought to reflux. After 8 h of reflux, the reaction mixture was subsequently cooled to 0° C., and ice cold 6N HCl solution (650 mL) was added. The reaction mixture was then stirred at ambient temperature for 8 h. After cooling, the reaction mixture was poured into a separatory funnel and washed with ether. The aqueous layer was then basified with $K_2CO_3$ and then extracted with chloroform. The organic extracts were combined, dried ($Na_2SO_4$), and concentrated to provide a dark brown oil. This material was purified on a Waters Delta Prep 3000 LC apparatus (10% hexanes-chloroform) to afford 19.4 g (93%) of desired benzophenone as a brown oil whose $^1$H NMR in $CDCl_3$ was consistent with the desired structure.

To a solution of this benzophenone (3.00 g, 7.76 mmol) in 75 mL of absolute ethanol was added sodium borohydride (0.35 g, 9.31 mmol). After 36 h of stirring under nitrogen, the reaction mixture was analyzed by thin layer chromatography which indicated a 90% conversion to product. Additional sodium borohydride (0.07 g) was added and stirring was continued for another 18 h. After cooling in an ice bath, 1N HCl solution (11 mL) was added. The resulting suspension was stirred for one minute and then was basified with solid $K_2CO_3$. This mixture was extracted with chloroform. The chloroform extracts were combined, dried ($Na_2SO_4$), and concentrated to provide 2.84 g of a white foam. This material was dissolved in methanol and perchloric acid (1.2 mL) was added. The solution was triturated with ethyl ether. The resultant solid was recrystallized from methanol/ethyl ether to afford 1.45 g (31%) of 5 diperchlorate as a cream-colored powder, mp 198°-210° C. The $^1$H NMR in $D_2O$ supported the assigned structure.

Elemental analysis: Calculated for $C_{25}H_{28}N_2O_2 \cdot 2.0HClO_4 \cdot 1H_2O$: C, 49.53; H, 5.31; N, 4.61; Cl, 11.67; $H_2O$, 2.97. Found C, 49.80; H, 5.56; N, 4.62; Cl, 11.66; $H_2O$, 5.36.

EXAMPLE 6

[3-[4-(2-Methoxyphenyl)-1-piperazinyl]methyl]-α-methyl-α-ethylbenzenemethanol (6)

To an ice-cooled solution of 1-(3-cyanobenzyl)-4-(2-methoxyphenyl)piperazine (20.0 g, 0.0649 mol) in 750 mL of tetrahydrofuran was added a solution of methylmagnesium bromide in ether (65.0 mL, 3.0M) under nitrogen. The solution was slowly warmed to 25° C. and then brought to reflux. After 8 h of reflux, thin layer chromatography indicated complete reaction. The reaction mixture was then cooled to 0° C., ice cold 6N HCl solution (600 mL) was added, and the reaction mixture was stirred at ambient temperature for 15 h. The reaction mixture was poured into a separatory funnel and washed with ether. The aqueous layer was then basified with $K_2CO_3$ and then extracted with chloroform. The organic extracts were combined, dried ($Na_2SO_4$), and concentrated to provide a dark brown oil. This material was purified on a Waters Delta Prep 3000 LC apparatus (10% hexanes-chloroform) to afford 16.0 g (76%) of expected methyl ketone as a brown oil whose $^1$H NMR in $CDCl_3$ was consistent with the desired structure.

A solution of the material prepared above (4.20 g, 12.9 mmol) in 150 mL of tetrahydrofuran was cooled to −78° C. under nitrogen, and a solution of ethylmagnesium bromide in ethyl ether (8.6 mL, 3.0M) was added. After stirring at −78° C. for 2 h, the reaction mixture was slowly warmed to 25° C. After 15 h of reflux, thin layer chromatography indicated that starting material had been completely consumed. The reaction mixture was then cooled to 0° C., and saturated bicarbonate solution was added. The resulting solution was then extracted with chloroform. The organic extracts were combined, dried ($Na_2SO_4$), and concentrated. The residue was purified on flash silica gel (10% hexanes-chloroform to 2.5% hexanes-chloroform) to afford a brown oil which consisted of the desired product in addition to a faster moving impurity by thin layer chromatography. This material was repurified by flash column chromatography on silica gel (10% hexanes-chloroform to 3% methanol-chloroform) to provide 2.35 g of a brown oil. This material was dissolved in methanol and fumaric acid (0.66 g) was added followed by trituration with ethyl ether. The resultant solid was recrystallized from acetone/ethyl ether to afford 1.62 g (30%) of 6 hemifumarate as a snow-white powder, mp 178.5°-179.5° C. The $^1$H NMR in $CD_3OD$ supported the assigned structure.

Elemental analysis: Calculated for $C_{22}H_{30}N_2O_2 \cdot 0.5C_4H_4O_4$: C, 69.88; H, 7.82; N, 6.79. Found C, 69.81; H, 8.14; N, 6.65.

EXAMPLE 7

[3-[4-(2-Methoxyphenyl)-1-piperazinyl]methyl]-α-(1-methylethyl)-benzenemethanol (7)

To an ice-cooled solution of 1-(3-cyanobenzyl)-4-(2-methoxyphenyl)piperazine (5.60 g, 18.2 mmol) in 250 mL of tetrahydrofuran was added a solution of isopropylmagnesium chloride in ethyl ether (27.3 mL, 2.0M) under nitrogen. The solution was slowly warmed to 25° C. and then brought to reflux. After 10 h of reflux, thin layer chromatography indicated that the reaction was complete. The reaction mixture was then cooled to 0° C., ice cold 6N HCl solution (200 mL) was added, and the reaction mixture was stirred at ambient temperature for 4 h. The reaction mixture was then poured into a separatory funnel and washed with ether. The aqueous layer was then basified with $K_2CO_3$ and then extracted with chloroform. To facilitate separation of the two layers, brine was added. The organic extracts were combined, dried ($Na_2SO_4$), and concentrated to provide a dark brown oil. This material was purified on flash silica gel (1% hexanes-chloroform to chloroform to 1% methanol-chloroform) to afford 4.08 g (64%) of the expected isopropyl ketone as a brown oil whose $^1H$ NMR in $CDCl_3$ was consistent with the desired structure.

To a solution of this ketone (3.90 g, 11.1 mmol) in 100 mL of ethanol was added sodium borohydride (0.50 g, 13.3 mmol). After 15 h of stirring under nitrogen, the reaction mixture was analyzed by thin layer chromatography which indicated that reaction was complete. After cooling in an ice bath, 1N HCl solution (15 mL) was added. The resulting suspension was stirred for one minute and then was basified with solid $K_2CO_3$. This mixture was extracted with chloroform. The chloroform extracts were combined, dried ($Na_2SO_4$), and concentrated. The residue was purified on flash silica gel (1% hexanes-chloroform to pure chloroform to 5% methanol-chloroform) to provide a pale green oil. This material was dissolved in methanol and fumaric acid (1.32 g) was added. The solution was triturated with ethyl ether. The resultant solid was recrystallized from acetone/ethyl ether to afford 0.90 g (19%) of alcohol 7 hemifumarate as a fluffy white powder, mp 160°–161° C. The $^1H$ NMR in $CD_3OD$ supported the assigned structure.

Elemental analysis: Calculated for $C_{22}H_{30}N_2O_2.0.5C_4H_4O_4.0.5H_2O$: C, 68.38; H, 7.89; N, 6.65; $H_2O$, 2.14. Found C, 68.25; H, 7.82; N, 6.63; $H_2O$, 1.92.

EXAMPLE 8

[3-[4-(2-Methoxyphenyl)-1-piperazinyl]methyl]-α-(cyclohexyl)-benzenemethanol (8)

To an ice-cooled solution of 1-(3-cyanobenzyl)-4-(2-methoxyphenyl)piperazine (5.60 g, 18.2 mmol) in 250 mL of tetrahydrofuran was added a solution of cyclohexylmagnesium chloride in ethyl ether (27.3 mL, 2.0M) under nitrogen. The solution was slowly warmed to 25° C. and then brought to reflux. After 48 h of reflux, thin layer chromatography indicated that the reaction was complete. The reaction mixture was then cooled to 0° C., ice cold 6N HCl solution (200 mL) was added, and the reaction mixture was stirred at ambient temperature for 3 h. The reaction mixture was then poured into a separatory funnel and washed with ether. The aqueous layer was then basified with $K_2CO_3$ and then extracted with chloroform. The organic extracts were combined, dried ($Na_2SO_4$), and concentrated to provide a dark green-brown oil. This material was purified on flash silica gel (1% methanol-chloroform) to afford 7.88 g (quantitative yield) of expected cyclohexyl ketone as a brown oil whose $^1H$ NMR in $CDCl_3$ was consistent with the desired structure.

To a solution of this ketone (4.60 g, 11.7 mmol) in 100 mL of absolute ethanol was added sodium borohydride (0.58 g, 15.2 mmol). After 15 h of stirring under nitrogen, the reaction mixture was analyzed by thin layer chromatography which indicated that a small amount of unreacted ketone remained. Additional sodium borohydride (0.1 g) was added to the reaction mixture, and stirring was continued for another 24 h. After cooling in an ice bath, 1N HCl solution (16 mL) was added. The resulting suspension was stirred for one minute and then was basified with solid $K_2CO_3$. This mixture was extracted with chloroform. The chloroform extracts were combined, dried ($Na_2SO_4$), and concentrated to provide a colorless foam. This material was dissolved in methanol and perchloric acid (1.40 mL) was added. The solution was triturated with ethyl ether and hexanes. The resultant solid was recrystallized from methanol/ethyl ether to afford 3.00 g (43%) of alcohol 8 diperchlorate as a white powder, mp 230°–240° C. (decomposition). The $^1H$ NMR in $DMSO-d_6$ supported the assigned structure.

Elemental analysis: Calculated for $C_{25}H_{34}N_2O_2.2HClO_4$: C, 50.43; H, 6.09; N, 4.70, Cl 11.90. Found C, 50.71; H, 6.22; N, 4.72, Cl 11.90.

EXAMPLE 9

[4-[4-(2-Methoxyphenyl)-1-piperazinyl]methyl]-α-phenylbenzenemethanol (9)

The hydrochloride salt of 2-methoxyphenyl piperazine (40.0 g; 0.175 mol) was suspended in 400 mL of tetrahydrofuran. To this solution was added 4-cyanobenzyl bromide (41.2 g, 0.210 mol) and triethylamine (73.1 mL, 0.525 mol). The resulting suspension was refluxed for 30 h. After cooling, the reaction mixture was poured into 1N HCl solution. The resulting solution was washed with ether, basified with solid $K_2CO_3$, and extracted with chloroform. The chloroform extracts were combined, dried ($Na_2SO_4$), and concentrated to provide a golden brown oil. Purification on a Waters Delta Prep 3000 LC apparatus afforded 51.3 g (95%) of a cream-colored solid whose spectral properties were consistent with the expected benzylarylpiperazine.

To an ice-cooled solution of 1-(4-cyanobenzyl)-4-(2-methoxyphenyl)piperazine (17.0 g, 55.3 mmol) in 800 mL of tetrahydrofuran was added a solution of phenylmagnesium bromide in ethyl ether (55.3 mL, 3.0M) under nitrogen. The solution was slowly warmed to 25° C. and then brought to reflux. After 48 h of reflux, the reaction mixture was subsequently cooled to 0° C., and ice cold 6N HCl solution (650 mL) was added. The reaction mixture was then stirred at ambient temperature for 2 h. After cooling, the reaction mixture was poured into a separatory funnel and washed with ether. The aqueous layer was then basified with $K_2CO_3$ and then extracted with chloroform. The organic extracts were combined, dried ($Na_2SO_4$), and concentrated to provide 25.5 g of a brown oil. This material was dissolved in methanol and concentrated hydrochloric acid was added. The solution was triturated with ethyl ether.

The resultant solid was recrystallized from methanol-/ethyl ether to afford 16.5 g (64%) of the expected benzophenone as a cream-colored powder, mp 260°-263° C. The $^1$H NMR in DMSO-$d_6$ supported the desired structure.

Elemental analysis: Calculated for $C_{25}H_{26}Cl_2N_2O_2 \cdot 2.0HCl \cdot 0.2H_2O$: C, 64.85; H, 6.18; N, 6.05; Cl, 15.31; $H_2O$, 0.78. Found C, 65.05; H, 6.20; N, 6.46; Cl, 15.19; $H_2O$, 0.68.

The free base of the benzophenone described above was prepared by treatment of the hydrochloride salt with bicarbonate followed by extraction into methylene chloride to provide a brown oil (4.30 g, 11.1 mmol). To a solution of this oil in 110 mL of absolute ethanol was added sodium borohydride (0.55 g, 14.5 mmol). After 16 h of stirring under nitrogen, the reaction mixture was analyzed by thin layer chromatography which indicated a 90% conversion to product. Additional sodium borohydride (0.10 g) was added, and stirring was continued for 1 h. After cooling in an ice bath, 1N HCl solution (16 mL) was added. The resulting suspension was stirred for one minute and then was basified with solid $K_2CO_3$. This mixture was extracted with chloroform. The chloroform extracts were combined, dried ($Na_2SO_4$), and concentrated to provide a yellow foam. Purification by flash silica gel chromatography (chloroform to 1% methanol/chloroform) afforded a white foam. This material was dissolved in acetone and fumaric acid (1.1 g) was added. The solution was triturated with ethyl ether. The resultant solid was recrystallized from acetone to afford 1.55 g (28%) of 9 fumarate as fluffy white crystals, mp 195°-196° C. (decomposition). The $^1$H NMR in DMSO-$d_6$ supported the assigned structure.

Elemental analysis: Calculated for $C_{25}H_{28}N_2O_2 \cdot C_4H_4O_4$: C, 69.03; H, 6.39; N, 5.55. Found C, 68.74; H, 6.37; N, 5.63.

$R^1$ and $R^2$ are independently selected from any of H, $C_1$-$C_8$ alkyl, $C_4$-$C_{10}$ cycloalkyl, $C_2$-$C_6$ hydroxyalkyl, $C_1$-$C_8$ alkoxyl, aryloxy, hydroxyl, trifluoromethyl, trifluoromethoxy, cyano, $C_1$-$C_8$ alkythio, halogen, nitro, $C_1$-$C_8$ haloalkyl, amino or $C_1$-$C_8$ mono- or di-alkylamino, with the proviso that $R^1$ and $R^2$ can not both be H at the same time;

variable n has a value of 1–4;

A is N;

$R^3$ is selected from any of H, $C_1$-$C_8$ acyl, $C_1$-$C_8$ alkyl, $C_4$-$C_8$ cycloalkyl or aralkyl wherein the alkyl portion is $C_1$-$C_8$;

$R^4$ and $R^5$ are independently selected from any of H, $C_1$-$C_8$ alkyl, phenyl, substituted phenyl, aralkyl wherein the alkyl portion is $C_1$-$C_8$, $C_4$-$C_8$ cycloalkyl; wherein the phenyl is substituted with one or more of $C_1$-$C_8$ alkyl, $C_1$-$C_8$ alkoxy, halogen, trifluoromethyl, $C_1$-$C_8$ alkylthio, dialkylamino (wherein each alkyl is $C_1$-$C_8$), $C_1$-$C_8$ alkylamino, nitro, or mono- or di-alkylamino sulfonyl (wherein each alkyl is $C_1$-$C_8$); $R^9$ and $R^{10}$ are independently selected from any one of H, $C_1$-$C_8$ alkyl, $C_1$-$C_8$ alkoxy, nitro, halogen, haloalkyl, $C_1$-$C_8$ alkylthio, amino, or $C_1$-$C_8$ mono- or di-alkylamino or a pharmaceutically acceptable salt thereof.

2. The compound of claim 1, wherein $R^1$ and $R^2$ are independently selected from either of alkoxy or H.

3. The compound of 2, wherein alkoxy is either i-propoxy or methoxy.

4. The compound of claim 1, wherein $R^4$ and $R^5$ are independently selected from any of phenyl, $C_1$-$C_5$ alkyl or cyclohexyl.

5. The compound of claim 4, wherein $R^4$ and $R^5$ are independently selected from either of phenyl or $C_1$-$C_5$ alkyl.

6. The compound of claim 2, wherein $R^4$ and $R^5$ are independently selected from any of phenyl, $C_1$-$C_5$ alkyl

TABLE 1

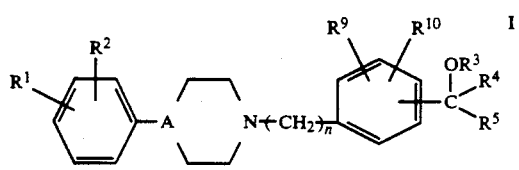

| Comp. # | $R^1$ | $R^2$ | $R^3$ | $R^4$ | $R^5$ | Substitution Pattern of $CH_2$ and $C(OR^3)R^4 R^5$ | CAR 5 mg/kg (IP) | Escape Loss | D-2 Binding K-I (nM) |
|---|---|---|---|---|---|---|---|---|---|
| 1 | 2-OiPr | H | H | Ph | H | 1,3 | −94.5 | 15 | 5 |
| 2 | 2-OiPr | H | H | Me | H | 1,3 | −66.5 | 0 | 56 |
| 3 | 2-OiPr | H | Ac | H | H | 1,3 | −86.0 | 38 | 51 |
| 4 | 2-OiPr | H | H | H | H | 1,3 | −89.2 | 13 | 302 |
| 5 | 2-OMe | H | H | Ph | H | 1,3 | −64.6 | 2 | 87 |
| 6 | 2-OMe | H | H | Et | Me | 1,3 | −86.0 | 2 | 198 |
| 7 | 2-OMe | H | H | iPr | H | 1,3 | −98.8 | 12 | 90 |
| 8 | 2-OMe | H | H | cHx | H | 1,3 | −92.9 | 2 | 16 |
| 9 | 2-OMe | H | H | Ph | H | 1,4 | −99.4 | 32 | 53 |

We claim:

1. A compound of the formula I:

or cyclohexyl.

7. The compound of claim 1, having the formula 3-[4-[2-(1-methylethoxy)phenyl]-1-piperazinylmethyl]-α-phenylbenzenemethanol.

8. The compound of claim 1, having the formula 4-[4-[2-(1-methylethoxy)phenyl]-1-piperazinylmethyl]-α-phenylbenzenemethanol.

9. The compound of claim 1, having the formula 3-[4-[2-(1-methylethoxy)phenyl]-1-piperazinylmethyl]-α-methyl-α-ethyl benzenemethanol.

wherein

10. The compound of claim 1, having the formula 1-(3-acetoxymethylphenyl)methyl-4-[2-(1-methylethoxy)phenyl]piperazine.

11. The compound of claim 1, wherein the relationship of the C(OR$^3$) R$^4$R$^5$ substituent with the —CH$_2$— group on the C(OR$^3$) R$^4$R$^5$ bearing phenyl ring is 1,3.

12. The compound of claim 1, wherein the relationship of the C(OR$^3$) R$^4$R$^5$ substituent with the —CH$_2$— group on the C(OR$^3$) R$^4$R$^5$ bearing ring is 1,4.

13. A composition comprising the compound of formula I as recited in claim 1, and a pharmaceutically acceptable carrier, said compound being present in a therapeutically effective amount.

14. A method of treating schizophrenia comprising administering to an animal in need of such treatment the compound of formula I as recited in claim 1 in an amount sufficient to treat such schizophrenia.

15. The method of claim 14, wherein R$^1$ and R$^2$ are independently selected from either of alkoxy or H.

16. The method of claim 15, wherein R$^4$ and R$^5$ are independently selected from any of phenyl, C$_1$–C$_5$ alkyl or cyclohexyl.

17. The method of claim 14, wherein the compound of formula I has the formula 3-[4-[2-(1-methylethoxy)phenyl]-1-piperazinylmethyl]-α-phenylbenzenemethanol.

18. The method of claim 17, wherein the compound for formula I has the formula 4-[4-[2-(2-methylethoxy)phenyl]-1-piperazinlymethyl]-α-phenylbenzenemethanol.

19. The method of claim 14, wherein the compound of formula I has the formula 3-[4-[2-(1-methylethoxy)phenyl]-1-piperazinylmethyl]-α-methyl-α-ethylbenzenemethanol.

20. The method of claim 14, wherein the compound of formula is 1-(3-acetoxymethylphenyl)methyl-4-[2-(1-methoxyethoxy)phenyl]piperazine.

* * * * *

UNITED STATES PATENT AND TRADEMARK OFFICE
CERTIFICATE OF CORRECTION

PATENT NO. : 5,332,743
DATED : July 26, 1994
INVENTOR(S) : Ellen W. Baxter and Allen B. Reitz It is certified that error appears in the above-indentified patent and that said Letters Patent is hereby corrected as shown below:

In Col. 5, Reaction Scheme 2 delete

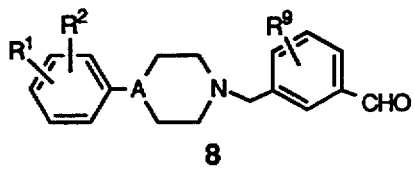

and replace with

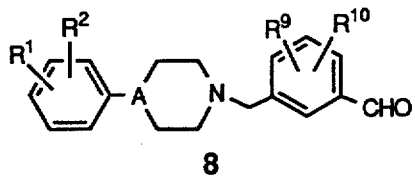

Signed and Sealed this

Twenty-eight Day of March, 1995

Attest:

BRUCE LEHMAN

Attesting Officer         Commissioner of Patents and Trademarks